US010112979B2

(12) United States Patent
O'Hagan

(10) Patent No.: US 10,112,979 B2
(45) Date of Patent: Oct. 30, 2018

(54) INFLUENZA VACCINATION

(71) Applicant: Seqirus UK Limited, Berkshire (GB)

(72) Inventor: Derek O'Hagan, East Hanover, NJ (US)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 14/673,644

(22) Filed: Mar. 30, 2015

(65) Prior Publication Data

US 2015/0299269 A1    Oct. 22, 2015

Related U.S. Application Data

(63) Continuation of application No. 11/667,055, filed as application No. PCT/US2005/039982 on Nov. 3, 2005, now abandoned.

(60) Provisional application No. 60/624,973, filed on Nov. 3, 2004.

(51) Int. Cl.

| C07K 14/11 | (2006.01) |
| A61M 37/00 | (2006.01) |
| C07K 14/005 | (2006.01) |
| A61K 39/145 | (2006.01) |
| A61K 39/12 | (2006.01) |
| A61K 9/00 | (2006.01) |
| C12N 7/00 | (2006.01) |
| A61K 39/00 | (2006.01) |

(52) U.S. Cl.
CPC .......... *C07K 14/005* (2013.01); *A61K 9/0021* (2013.01); *A61K 39/12* (2013.01); *A61K 39/145* (2013.01); *A61M 37/0015* (2013.01); *C12N 7/00* (2013.01); *A61K 2039/54* (2013.01); *A61K 2039/545* (2013.01); *A61K 2039/55* (2013.01); *A61K 2039/55505* (2013.01); *A61K 2039/70* (2013.01); *A61M 2037/0046* (2013.01); *A61M 2037/0061* (2013.01); *C12N 2760/16034* (2013.01); *C12N 2760/16134* (2013.01); *C12N 2760/16234* (2013.01)

(58) Field of Classification Search
CPC .. A61K 39/145; A61K 9/0021; A61K 9/7084; A61K 2039/5252; A61M 37/0015; A61M 5/14248; A61M 5/158; A61M 2037/0061; A61M 5/46; A61M 2037/0046; A61M 37/00; A61M 5/3295; A61M 2201/055; A61M 2037/0023; A61M 2202/30; B81B 2201/055; Y10T 156/10; C12N 2760/16111; C12N 2760/16211; C12N 2760/18434; C12N 2760/20034; C12N 2760/20134; C12N 2770/32634; C12N 2770/36234; C12N 2760/16134; C12N 2760/16234; C12N 2760/16034
See application file for complete search history.

(56) References Cited

U.S. PATENT DOCUMENTS

| 5,776,468 | A | 7/1998 | Hauser et al. |
| 6,334,856 | B1 | 1/2002 | Allen et al. |
| 6,451,325 | B1 | 9/2002 | Van Nest et al. |
| 6,843,781 | B2 * | 1/2005 | Alchas ................... A61M 5/46 604/117 |
| 7,316,813 | B2 | 1/2008 | Eichhorn |
| 7,588,774 | B2 | 9/2009 | Campbell et al. |
| 8,673,613 | B2 | 3/2014 | Jin et al. |
| 2004/0071734 | A1 | 4/2004 | Garcon et al. |
| 2004/0096463 | A1 | 5/2004 | Garcon et al. |
| 2005/0123550 | A1 * | 6/2005 | Laurent ................ A61K 9/0021 424/184.1 |
| 2005/0220854 | A1 | 10/2005 | Maa et al. |
| 2005/0255121 | A1 * | 11/2005 | Campbell ............ A61K 9/0021 424/184.1 |

FOREIGN PATENT DOCUMENTS

| CA | 1122527 A1 | 4/1982 |
| CA | 2235257 A1 | 4/1997 |
| WO | WO-90/14837 A1 | 12/1990 |
| WO | WO-97/37000 A1 | 10/1997 |
| WO | WO 02/07813 A1 | 1/2002 |
| WO | WO-02/074336 A2 | 9/2002 |
| WO | WO-02/085446 A2 | 10/2002 |
| WO | WO-03/002069 A2 | 1/2003 |
| WO | WO-03/076601 A1 | 9/2003 |
| WO | WO 2005/016239 A2 | 2/2005 |
| WO | WO 2005/099751 A2 | 10/2005 |

OTHER PUBLICATIONS

Chen et al. Expert Rev. Vaccine, 2002, 1(3), pp. 265-276.*
Stratum Corneum Defintions Searched by examiner in internet on 2006, pp. 1-3.*
CDC MMWR, Quick Guide, Recommendations and Reports published on Jan. 31, 2003; Q1-Q4, pp. 1-5.*
CDC MMWR, Recommendations and Reports published on May 28, 2004/53 (RR06); 1-40. pp. 1-51.*
Arora et al. (2008). "Micro-scale devices for transdermal drug delivery," Int J Pharm, 364(2):227-36.

(Continued)

*Primary Examiner* — Bao Q Li
(74) *Attorney, Agent, or Firm* — Finnegan, Henderson, Farabow, Garrett & Dunner, LLP

(57) ABSTRACT

Influenza viruses have traditionally been administered by intramuscular injection. The invention is based on the idea of using alternative routes of delivery for influenza vaccines, more specifically routes that do not require as large a dose of antigen. Delivery of influenza antigen to the Langerhans cells is the route of choice according to the invention. This route has been found to be particularly useful for vaccinating patients who are naïve to influenza virus (i.e. have not previously mounted an immune response to an influenza virus), which means that it is advantageous for immunising young children.

20 Claims, No Drawings

(56) References Cited

OTHER PUBLICATIONS

Aymard et al., "Rapid serodiagnosis of influenza by a modified radial haemolysis test: immune response," Path. Biol., vol. 28, No. 8, pp. 535-539, 1980.
Belshe et al., "Safety, efficacy and effectiveness of cold-adapted, live, attenuated trivalent, intranasal influenza vaccine in adults and children," Philosophical Transactions Roy. Soc. London Series B, vol. 356, pp. 1947-1951, Dec. 2001.
Bruhl et al. (2000). "Humoral and cell-mediated immunity to vero cell-derived influenza vaccine," Vaccine, 19(9-10):1149-58.
Carmona et al. (2010) "Immunogenicity and safety of AS03-adjuvanted 2009 influenza A H1N1 vaccine in children 6-35 months," Vaccine 28:5837-5844.
Centers for Disease Control and Prevention (Jul. 13, 2007). MMWR, 56:1-53.
Chen et al. (2004). "Epidermal powder immunization: cellular and molecular mechanisms for enhancing vaccine immunogenicity," Virus Research 103(1-2): 147-153.
Chen et al. (2001). "Serum and Mucosal Immune Responses to an Inactivated Influenza Virus Vaccine Induced by Epidermal Powder Immunization," Immunization, 75(17):7956-7965.
Commitiee for Proprietary Medicinal Products, "Note for guidance on harmonisation of requirements for influenza vaccines," PMP/BWP/214/96, Mar. 1997, pp. 1-18.
Cormier et al. (2003). "Macroflux technology for transdermal delivery of therapeutic proteins and vaccines, Chapter 48 in Modified-Release Drug Delivery Technology," Rathbone et al (Eds),. New York: Marcel Dekker; pp. 589-598.
Cormier et al. (2004). "Transdermal delivery of desmopressin using a coated microneedle array patch system," Journal of controlled release: official journal of the Controlled Release Society, 97( 3):503-11.
Daddona (2002). "Macroflux transdermal technology development for the delivery of therapeutic peptides and proteins," Drug Delivery Technology, 2(5):54-57.
Demicheli et al. (2006). "The Cochrane collaboration: Vaccines for preventing influenza in healthy children (Review)," *The Cochrane library*, Issue 3.
ECDC (Jan. 2007). "Technical report on the scientific panel on Vaccines and immunization: Infant and children seasonal immunization against influenza on a routine basis during inter-pandemic period." Stockholm.
Esposito et al. (2011) "Influenza A/H1N1 MF59-adjuvanted vaccine in preterm and term children aged 6 to 23 months," Pediatrics 127(5):e1161-e1168.
Extended European Search Report dated Oct. 1, 2007, for EP application No. 05823432.9, filed Nov. 3, 2005, 5 pages.
Ferguson et al. (2003). "Ecological and immunological determinants of influenza evolution," Nature, 422(6930):428-33.
Garcia-Sicilia et al. (2011) "Immunogenicity and safety of AS03-adjuvanted H1N1 pandemic vaccines in children and adolescents," Vaccine 29:4353-4361.
Garcon et al. (2012). "Development and evaluation of AS03, an adjuvant system containing α-tocopherol and squalene in an oil-in-water emulsion," Expert Rev. Vaccines 11(3):349-366.
Ghendon et al. (2006). "The effect of mass influenza immunization in children on the morbidity of the unvaccinated elderly," Epidemiol Infect, 134(1):71-8.
Gilca et al. (2011) "Effectiveness of pandemic H1N1 vaccine against influenza-related hospitalization in children," Pediatrics 128:e1084-e1091.
Halperin et al. (1979). "A comparison of the intradermal and subcutaneous routes of influenza vaccination with A/New Jersey/76 (swine flu) and A/Victoria/75: report of a study and review of the literature," Am J Public Health, 69(12):1247-51.
Hehme et al. (2002). "Ten Years of Experience with the Trivalent Split-Influenza Vaccine, Fluarix™." Clinical Drug Investigation, 22(11): 751-769.
Heikkinen et al. (2004). "Burden of influenza in children in the community," J Infect Dis. 190(8):1369-73.

Higgins et al. (1996). "MF59 adjuvant enhances the immunogenicity of influenza vaccine in both young and old mice," Vaccine, 14(6):478-84.
International Search Report dated Jun. 26, 2006 for PCT Application No. PCT/US05/39982 filed Nov. 3, 2005.
Iskander et al. (2007). "The burden of influenza in children," Curr Opin Infect Dis, 20(3):259-63.
Izurieta et al. (2000). "Influenza and the rates of hospitalization for respiratory disease among infants and young children," N Engl J Med, 342(4):232-9.
Jefferson et al. (2010) "The Cochrane collaboration: Vaccines for preventing influenza in healthy children (Review)," Cochrane Database of Systematic Reviews 2008, Issue 2. (summary).
Knipe & Howley, Orthomyxoviridae (2004). "The Viruses and Their Replication," in Fields Virology, 4th Edition, Ch. 46, pp. 1487-1531.
Koelle et al. (2006). "Epochal evolution shapes the phylodynamics of interpandemic influenza A (H3N2) in humans," Science, 314(5807):1898-903.
Kommareddy (2013). "Influenza subunit vaccine coated microneedle patches elicit comparable immune responses to intramuscular injection in guinea pigs." Vaccine. 31(34):3435-41.
Koutsonanos et al., Additional Data, Submitted on Jul. 30, 2014 during prosecution for EP1807116, 4 pages.
Kumagai et al. (2004). "Poor immune responses to influenza vaccination in infants," Vaccine, 22(25-26):3404-10.
Latebreaking Abstracts: Late Breaker Poster (Oct. 23, 2010). "Intradermal 2009 Pandemic Influenza A(H1N1) Vaccination as a Strategy for Dose and Adjuvant Sparing." 3 pages.
Lazar et al. (1980). "Humoral and cellular immune responses of seronegative children vaccinated with a cold-adapted influenza A/HK/123/77 (H1N1) recombinant virus," Infect Immun, 27(3):862-6.
Louie et al. (2006). "Severe pediatric influenza in California, 2003-2005: implications for immunization recommendations," Pediatrics, 117(4):e610-8.
Maa et al. (2004). "Influenza vaccine powder formulation development: Spray-Freeze-Drying and Stability evaluation," J. Pharm. Sci, 93(7)1912-1923.
Matriano et al. (2002). "Macroflux microprojection array patch technology: a new and efficient approach for intracutaneous immunization," Pharm Res, 19(1):63-70.
Mikszta et al. (Apr. 2002). "Improved genetic immunization via micromechanical disruption of skin-barrier function and targeted epidermal delivery," Nature Medicine 8, 415-419.
Mitchell et al. (2005). "Immunogenicity and safety of inactivated influenza virus vaccine in young children in 2003-2004," Pediatr Infect Dis J, 24(10):925-7.
Mitragotri (2005). "Immunization without needles," Nat Rev Immunol, 5(12):905-16.
Neuzil et al. (2000). "The effect of influenza on hospitalizations, outpatient visits, and courses of antibiotics in children," N Engl J Med, 342(4):225-31.
Novartis International AG, (Oct. 22, 2010). "Novartis Phase III study indicates MF59® adjuvanted influenza vaccine, Fluad®, is 75 percent more efficacious than studied non-adjuvanted vaccines in young children," Novartis Media Release, 4 pages.
O'Hagan, ed. (2000). "Vaccine Adjuvants: Preparation Methods and Research Protocols, Volume 42 of Methods in Molecular Medicine series," ISBN: 1-59259-083-7.
Palmer et al. (1975). "Advanced laboratory technicals for immunological diagnostics," Immunology ser. Nr. 6, Procedural guide, pp. 25-62.
Park et al. (Sep. 1-5, 2004). "Biodegradable polymer microneedles: fabrication, mechanics and transdermal drug delivery," Proceedings of the 26th Annual International Conference of the IEEE EMBS, San Francisco, CA, pp. 2654-2657.
Pau et al. (2001). "The human cell line PER.C6 provides a new manufacturing system for the production of influenza vaccines," Vaccine, 19(17-19):2716-21.
Peltola et al. (2003). "Influenza A and B virus infections in children," Clin Infect Dis, 36(3):299-305.

(56) References Cited

OTHER PUBLICATIONS

Petrovsky et al. (Aug. 2, 2007) "New-Age Vaccine Adjuvants: Friend or Foe? A major unsolved challenge in adjuvant development is how to achieve a potent adjuvant effect while avoiding reactogenicity or toxicity," downloaded Dec. 18, 2011 from Biopharminternational.com.
Piascik, "Intranasal Flu Vaccine Available This Season," J. Am. Pharm. Assoc., vol. 43, pp. 728-730, 2003.
Plotkin & Orenstein, eds., (2004). "Vaccines," 4th edition, ISBN: 0-7216-9688-0.
Podda (2001). "The adjuvanted influenza vaccines with novel adjuvants: experience with the MF59-adjuvanted vaccine," Vaccine, 19(17-19):2673-80.
Podda (2003). "MF59-adjuvanted vaccines: increased immunogenicity with an optimal safety profile," Expert Rev Vaccines, 2(2):197-203.
Poehling et al. (2006). "The underrecognized burden of influenza in young children," N Engl J Med, 355(1):31-40.
Powell & Newman, eds. (1995). "Vaccine Design: The Subunit and Adjuvant Approach Plenum Press," ISBN 0-306-44867-X.
Prausnitz (2004). "Microneedles for transdermal drug delivery," Advanced Drug Delivery Reviews, 56(5):581-587.
Principi et al. (2003). "Socioeconomic impact of influenza on healthy children and their families," Pediatr Infect Dis J, 22(10 Suppl):S207-10.
Schild et al. (1975). "Single radial haemolysis: a new method for the assay of antibody to influenza haemagglutinin," Bull. World Health Org., 52 (43-50).
Skowronski et al. (2007). "Estimating vaccine effectiveness against laboratory-confirmed influenza using a sentinel physician network: results from the 2005-2006 season of dual A and B vaccine mismatch in Canada," Vaccine, 25(15):2842-51.
Sugimura et al. (2008). "Improved antibody responses in infants less than 1 year old using intradermal influenza vaccination," Vaccine. 26(22):2700-5.
Treanor et al. (1996). "Evaluation of a recombinant hemagglutinin expressed in insect cells as an influenza vaccine in young and elderly adults," J Infect Dis, 173(6):1467-70.
Vesikari et al. (2009) "Enhanced immunogenicity of seasonal influenza vaccines in young children using MF59 adjuvant," Pediatric Infectious Disease Journal 28(7):563-571.
Vesikari et al. (2011) "Oil-in-water emulsion adjuvant with influenza vaccine in young children," New England Journal of Medicine 365(15):1406-1416.
Walter et al. (2006). "Influenza vaccine immunogenicity in 6- to 23-month-old children: are identical antigens necessary for priming?" Pediatrics, 118(3):e570-8.
Wollenberg et al. (2002). "Plasmacytoid dendritic cells: a new cutaneous dendritic cell subset with distinct role in inflammatory skin diseases," J Invest Dermatol, 119(5):1096-102.
Chen et al. (2000). "Epidermal immunization by a needle-free powder delivery technology: immunogenicity of influenza vaccine and protection in mice." Nat Med, 6(10):1187-90.
Glezen et al., "Influenza virus infections in infants," Pediatr Infect Dis J, 16(11):1065-1068, (1997).
Kemble et al., "Novel generations of influenza vaccines," Vaccine, 21(16):1789-1795, (2003).
Kitler et al., "Influenza and the work of the World Health Organization," Vaccine, 20 Suppl 2:S5-S14, (2002).
Mischler et al., "Inflexal® V a trivalent virosome subunit influenza vaccine: production," Vaccine, 20 Suppl 5:B17-B23, (2002).
Partidos, "Delivering vaccines into the skin without needles and syringes," Expert Rev Vaccines, 2(6):753-761, (2003).
Sullivan et al., "Dissolving polymer microneedle patches for influenza vaccination," Nat Med, 16(8):915-920, (2010).
To et al., LB-19 Abstract, "Intradermal 2009 Pandemic Influenza A (H1N1) Vaccination as a Strategy for Dose and Adjuvant Sparing," 48th Annual Meeting of the Infectious Diseases Society of America, Vancouver, (2010).
Influenza Pandemic Plan. The Role of WHO and Guidelines for National and Regional Planning, World Health Organization, Geneva, Switzerland, (1999).
MMWR Recommendations and Reports, Prevention and Control of Influenza: Recommendations of the Advisory Committee on Immunization Practices (ACIP), 51(RR03), (2002).
Opposition Decision for EP Application No. 05 823 432.9-1410, dated Oct. 25, 2017.
The Second International Conference on Modern Vaccines Adjuvants & Delivery Systems, Second Circular and Provisional Conference Programme, The Royal Society of Medicine, London, UK, (2006).
Vaxigrip®, "Inactivated Influenza Vaccine Trivalent Types A and B (Split Virion)," 9 pages, product insert, (2004).

* cited by examiner

INFLUENZA VACCINATION

CROSS REFERENCE TO RELATED APPLICATIONS

This application is a Continuation of U.S. patent application Ser. No. 11/667,055, with an international filing date of Nov. 3, 2005; which is a National Phase of International Patent Application No. PCT/US2005/039982, filed Nov. 3, 2005; which claims the benefit of U.S. Provisional Patent Application Nos. 60/624,973, filed Nov. 3, 2004, all of which are incorporated herein by reference in their entirety.

FIELD OF THE INVENTION

This invention concerns influenza virus vaccines, and in particular pediatric vaccines for delivery to the Langerhans cells.

BACKGROUND ART

In the past, influenza vaccines have generally been administered to patients at particular risk from the consequences of influenza infection, such as: children with asthma, cardiac disease, sickle cell disease, HIV or diabetes; children living in a household containing someone suffering from asthma, cardiac disease, sickle cell disease, HIV or diabetes; and the elderly.

More recently, there have been suggestions that the scope of influenza vaccination should be extended to include all children, rather than just those at high risk. To increase coverage in this way, however, would require a huge increase in production capacity, and vaccine manufacturers are not well placed to deliver this increase. Stockpiling of vaccines is not possible because the vaccine strains change every year and are produced almost in a just-in-time manner.

Thus there is a need to increase the available doses of influenza vaccine in order to deal with the increased demand for pediatric vaccination.

DISCLOSURE OF THE INVENTION

Influenza viruses have traditionally been administered by intramuscular injection, although more recently an intranasal vaccine has been approved for human use [1]. The invention is based on the idea of using alternative routes of delivery for influenza vaccines, more specifically routes that do not require as large a dose of antigen. Delivery of influenza antigen to the Langerhans cells is the route of choice according to the invention. This route has been found to be particularly useful for vaccinating patients who are naïve to influenza virus (i.e. have not previously mounted an immune response to an influenza virus), which means that it is advantageous for immunising young children. Moreover, delivery to Langerhans cells may offer improved heterosubtypic immunity compared to intramuscular injection.

As well as increasing the number of vaccine doses that can be produced from a given amount of antigen, a move away from intramuscular injection means that the invention avoids the pain associated with influenza vaccination, thereby increasing both patient comfort and compliance.

Therefore the invention provides a method for immunising a patient against influenza virus, comprising the step of administering an immunogenic composition to the patient, wherein: (a) the patient is naïve to influenza virus; (b) the immunogenic composition comprises an influenza virus antigen; and (c) the immunogenic composition is delivered to the patient's Langerhans cells.

The invention also provides the use of an influenza virus antigen in the manufacture of a medicament for immunising a patient against influenza virus, wherein: (a) the patient is naïve to influenza virus; and (b) the medicament is for delivery to the patient's Langerhans cells.

The invention also provides an immunogenic composition comprising an influenza virus antigen, wherein the composition is adapted for delivery to Langerhans cells.

The invention also provides a delivery device wherein: (a) the delivery device includes an immunogenic composition; (b) the immunogenic composition comprises an influenza virus antigen; and (c) the delivery device is adapted to deliver the immunogenic composition to Langerhans cells.

The Patient

The invention is concerned with immunisation of patients who are immunologically naïve to influenza virus. In other words, the patients have not previously mounted an immune response to influenza virus. The patients will not previously have been infected by as influenza virus and will not have been immunised against influenza virus. Typically, therefore, the patient is a child aged between 0 and 18 months, more usually between 0 and 12 months, and often between 0 and 6 months. The most preferred age at which vaccination according to the invention takes place is between 4 and 8 months e.g., between 5 and 7 months, or at about 6 months old.

In an alternative aspect of the invention, the patient may previously have mounted an immune response to au influenza virus, but they will be immunologically naïve in relation to the influenza genus (i.e. influenza A or B virus) and/or subtype (H or N, but particularly the H subtype) of the administered vaccine. Such a patient may be a child (aged between 0 months and 12 years), a teenager (aged between 13 and 19 years), a young adult (aged between 20 and 35 years), a middle aged adult (aged between 36 and 64 years), or a senior (aged 65 year and older).

The patient may already have received vaccines against one or more (i.e. 1, 2, 3, 4, 5, 6 or 7) of diphtheria, tetanus, pertussis *Haemophillus influenzae* type b, hepatitis B virus, poliovirus and/or *Streptococcus pneumoniae*.

The patient will generally not already have received vaccines against any of measles, mumps, rubella, varicella, or hepatitis A virus.

The patient preferably does not have asthma, cardiac disease, sickle cell disease, HIV or diabetes. Similarly, the patient preferably does not live in a household that contains anyone suffering from asthma, cardiac disease, sickle cell disease, HIV or diabetes.

The Influenza Virus and the Influenza Virus Antigens

The uses influenza virus antigens to immunise against influenza virus infection. The specific virus from which the antigens are derived may be the same as or different from the specific virus for which protection is being provided, because cross-protection between different isolates is known to occur with influenza viruses, particularly within the same viral subtypes.

Moreover, the invention may use antigens more than one influenza virus, in order to immunise against more than one influenza virus. Vaccine strains for influenza virus change from season to season. In the current inter-pandemic period, vaccines typically include two influenza A strains (H1N1, and H3N2) and one influenza B strain. Thus the invention may use antigens from at least, one strain of influenza A virus and/or at least one strain of influenza B virus. Trivalent vaccines are preferred. The invention may also use viruses from pandemic strains, such as H2, H5, H7 or H9 subtype strains, that is strains to which the general human population is immunologically naïve. Vaccines in pandemic situations may be monovalent, or they may be based on a normal trivalent vaccine supplemented by a pandemic strain.

Where a vaccine includes more than one strain of influenza, the different strains are typically grown separately and are mixed after the viruses have been harvested and antigens have been prepared.

The influenza virus(es) used in the processes of the invention may be reassortant strains, and/or may have been obtained by revere genetics techniques. The virus(es) may be attenuated. The virus(es) may be temperature-sensitive. The virus(es) may be cold-adapted. A reassortant strain including the HA and/or NA viral segments from a pathogenic strain and the remaining six or seven segments from a non-pathogenic strain (e.g. A/PR/8/34) may be used.

The influenza virus antigen used in the immunogenic composition according to the invention may be in the form of a live virus or, preferably, an inactivated virus. Virus inactivation typically involves treatment with as chemical such as formalin or β-propiolactone. Where an inactivated virus is used, the antigen may be a whole virus, a split virus, or viral subunits. Split viruses are obtained by treating virions with detergents (e.g. ethyl ether, polysorbate 80, deoxycholate, tri-N-butyl phosphate, Triton X-100, Triton N101, cetyltrimethylammonium bromide, etc.) to produce subvirion preparations. Subunit vaccines comprise one or both of the influenza surface antigens haemagglutinin and neuraminidase. Influenza antigens can also be presented in the form of virosomes [2].

Where an antigen is prepared from, an influenza virus (i.e. rather than having been produced in a recombinant or synthetic system that does not involve growth of influenza viruses), the virus may be grown either on eggs or in cell culture. Growth in specific pathogen free embryonated eggs is the traditional route by which influenza viruses have been gown for vaccine production, and cell culture is a more recent development. Where cell culture is used then the influenza virus vaccine will typically be grown on mammalian cells, such as MDCK cells [3-6], Vero cells [7-9] or PER.C6 cells [10]. These cell lines are widely available e.g. from the American Type Cell Culture (ATCC) collection [11], or from the Coriell Cell Repositories [12]. For example, the ATCC, supplies various different Vero cells under catalog numbers CCL-81, CCL-81.2, CRL-1586 and CRL-1587, and it supplies MDCK cells trader catalog number CCL-34. Growth on avian cell lines [e.g. ref, 13], including cell lines derived from hens e.g. chicken embryo fibroblasts (CEF), is also possible.

The Immunogenic or Medicament Composition

Immunogenic and medicament compositions of the invention are suitable for administration to the Langerhans cells of a patient. This can be achieved by various ways, including but not limited to: intradermal injection [14,15]; transdermal administration [16]; and topical administration. These may be used in conjunction with skin abrasion e.g. by emery paper or by the use of microabrasives. immunogenic and medicament compositions of the invention are preferably presented as vaccines.

Compositions of the invention may include an adjuvant. Adjuvants that have been used in influenza vaccines include aluminium salts [17,18], chitosan [19]. CpG oligodeoxynucleotides such as CpG 7909 [20] oil-in-water emulsions such as MF59 [21], water-in-oil-in-water emulsions [22], E. coli heat labile toxin [23,24] and its detoxified mutants [25,26], monophosphoryl lipid A [27] and its 3-o-deacylated derivative [28], pertussis toxin mutants [29], muramyl dipeptides [30], etc. For delivery to Langerhans cells, adjuvants that function by physical mechanisms are not preferred (e.g. emulsions and aluminium salts); instead, it is preferred to use immunopotentiating adjuvants e.g. those that function by binding to cell-surface receptors, such as CpG oligodeoxynucleotides.

Haemagglutinin (HA) is the main immunogen in inactivated influenza vaccines, and vaccines doses are standardised by reference to HA levels, typically as measured by a single radial immunodiffusion (SRID) assay [31,32]. Vaccines for intramuscular injection typically contain about 15 μg of HA per strain, although lower doses are also used (e.g. for children, or in pandemic situations) and fractional doses such as ½, (i.e. 7.5 μg HA per strain), ¼ and ⅛ have been used [17,33]. Administration to Langerhans cells does not require as much antigen as intramuscular injection, however, and so compositions of invention will typically include between 0.1 and 8 μg of HA per influenza strain, preferably e.g. about 7.5, about 5, about 3, about 2.5, about 2, about 1.5, about 1, about 0.75, about 0.5, about 0.4, about 0.2, etc.

Vaccines for intramuscular injection typically have a volume of 0.5 ml. Administration to Langerhans cells does not require as great a volume a intramuscular injection, however, and so compositions of the invention will typically have a volume of between 0.05 and 0.5 ml e.g. between 90 μl and 250 μl.

The compositions may include preservatives such as thiomersal or 2-phenoxyethanol. It is preferred, however, that the compositions should be substantially free from (i.e. less than 1 μg/ml) mercurial material e.g. thiomersal-free [34,35]. Vaccines containing no mercury are more preferred.

Where influenza virus has been grown on cell culture then compositions of the invention preferably contain less than 100 pg of residual host cell DNA per dose, although trace amounts a host cell DNA may be present, Contaminating DNA can be removed during vaccine preparation using standard purification procedures e.g. chromatography, etc. Removal of residual host cell DNA can be enhanced by nuclease treatment e.g. by using the Benzonase™ DNase. [36]. Vaccines containing <100 pg host cell DNA per 10 μg of haemagglutinin are preferred, as are vaccines containing <100 pg host cell DNA per 0.25 ml volume. Vaccines containing <100 pg host cell DNA per 50 μg of haemagglutinin are more preferred, as are vaccines containing <100 pg host cell DNA per ml volume.

The vaccines of the invention may be delivered as a single dose immunization regimen. Alternatively, they may be delivered as the prime element of a prime-boost regimen (meaning that the first immunization is followed by a second shot of similar antigenicity within a few weeks or months).

Delivery to Langerhans Cells

Langerhans cells are highly specialised myeloid antigen-presenting cells (APCs) located in the skin, mucosa, and lymphoid tissues. The Langerhans cells originate in the bone marrow and migrate to the epidermis, where they form a regularly ordered network that earl reach a density of 700 to 800 cells per $mm^2$, covering up to 25% of total skin surface area in humans. The cells are easily recognised in electron microscope images as they contain characteristic intracellular cytoplasmic organelles resembling tennis rackets, known as the "Langerhans-granula" or "Birbeck granules". Langerhans cells are rich in Class II MHC. They can specifically activate dormant T-helper cells and thus initiate a primary T-cell dependent immune response. After contact with an antigen the cell can leave the epidermis and reach a lymph node via the lymphatic system. On it journey the cell will undergoes a maturation process leading to the presentation of the antigen on the cell surface. The migrating cells are replaced by a corresponding number of new Langerhans cells from the bone marrow. In the lymph nodes the mature Langerhans' cells activate the T-helper cells that have the matching antigen-specific receptors on their surfaces. In this way they steer the reaction of the immune system.

The invention is primarily concerned with delivering antigen to Langerhans cells within the epidermis. The epidermis is the outer layer of skin and contains 5 layers, these being (moving outwards): stratum hale, stratum spinosum, stratum granulosum, stratum licidum, and the outer stratum corneum. Langerhans cells are situated mainly within the stratum spinosum and/or stratum germinativum, beneath the stratum corneum.

Delivery to Langerhans cells can be achieved in various ways, using a variety of delivery devices. Delivery into the epidermis is preferred, although delivery into the dermis (e.g. intradermal delivery) still allows contact with the Langerhans cells.

Delivery can be achieved using devices that create micropores in the stratum corneum ("microporation"). Such devices include microstructures (sometimes called microneedles, which is now an accepted term in the art [37-40]) that, when applied to the skin, painlessly create micropores in the stratum corneum without causing bleeding (e.g. 3M's Microstructured Transdermal System, the Micropyramid™ system from NanoPass, etc.). The microneedles can be used singly or in a plurality (e.g. in an array [41]). The microneedles open pores in the stratum corneum and can take various sizes e.g. ranging in length from 25 μm to 1 mm. They are preferably small enough not to penetrate into the dermis and so not to reach the nerve endings, thereby avoiding any sensation of pain. The structures can be either solid (serving as a pretreatment prior to antigen application), solid with antigen coated directly on the outside of the needles, or hollow to facilitate fluidic transport through the needles and into the lower epidermis. They can be made from materials including, but not limited to: silicon, biodegradable polymers, metals (e.g. stainless steel, gold, etc.), and glass. Biodegradable polymers are safe even if needles snap off while inserted. The micropores produced by these devices offer lower resistance to drug diffusion than normal skin without micropores [42], and the systems have been reported to greatly enhance (up to 100,000 fold) the permeation of macromolecules through skin [43]. Vibratory actuation can be used in order to reduce the insertion force [44].

Similarly, a microprojection array system can be used (e.g. the Macroflux™ system from Alza). The projections can have a length of about 100-500 μm, with 50-500 microprojections per $cm^2$, over a 1-2 $cm^2$ area) and will typically be coated with antigens. These systems can delivery up to 80 μg of protein at an average depth of 100 μm, with no projections deeper than 300 μm [45]. Delivery rates can be as high as 20 μg in 5 seconds. Antigen can be dry-coated, with or without an adjuvant.

Microabrasive systems can be used.

Laser systems can be used to ablate the stratum corneum from the epidermal layer [46]. As with microneedles, the ablated regions offer lower resistance to drug diffusion than non-ablated skin.

Iontophoresis and sonophoresis can be used to increase flux across the stratum corneum. These systems can achieve significant skin permeation enhancement, including for proteins [47,48], particularly in the absence of hair.

Skin can optionally be abrased prior to administration of a composition e.g. using emery paper.

Thus compositions can be delivered to Langerhans cells by intradermal administration, transdermal administration, epidermal administration, topical administration (particularly after abrasion), etc. Delivery devices of the invention therefore include devices adapted for delivery by these routes.

Immunogenicity Testing

Methods for testing the immunogenicity of influenza vaccines are well known in the art. One method involves the following procedure: (a) just prior to vaccination, a 10 ml venous blood sample is taken from a patient, normally from the arm, for base-line titration of circulating anti-HA antibodies; (b) Immediately thereafter, a patient receives 1 dose of vaccine which, if administered to the arm, shall be given into the opposite arm from which blood was drawn; (c) Approximately 3 weeks after vaccination, a 10 ml blood sample shall be taken from patients. Sera are separated from the blood samples and stared (if necessary) at −20° C. Sera are assayed for anti-haemagglutinin antibody against the relevant strains, by hemagglutination inhibition (HI [49]) or single radial hemolysis (SRH [50,51]). Positive and negative sera as well as reference preparations can be obtained from public reference laboratories. Antibody titrations are performed in duplicate, and pre- and post-vaccination sera are titrated simultaneously. The titter assigned to each sample is the geometric mean of two independent determinations (but, for the purposes of calculation, any HI result <10 (=undetectable) is expressed as 5 and any negative SRH result is expressed as 4 $mm^2$ under standard conditions).

In HI tests, seroconversion corresponds to a ratio of pre- and post-immunization titers of ≥40 and a significant (e.g. at least 4-fold) increase in antibody titer. In SRH tests, seroconversion corresponds to a post-vaccination area ≥25 $mm^2$, with at least a 50% in area relative to the pre-vaccination area.

Preferred vaccines of the invention cause seroconversion of patients according to the tests set out in reference 52.

General

The term "comprising" encompasses "including"as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Further general information on influenza vaccines, including strains, cell lines for growth, doses, combinations, formulations, etc. can be found in chapters 17 & 18 of reference 53. Further details on influenza virus, including details of its life cycle during viral growth, can be found in chapter 46 of reference 54.

MODES FOR CARRYING OUT THE INVENTION

Pediatric Immunization

A trivalent vaccine is prepared from influenza virus strains A/New Caledonia/20/99 (H1N1), A/Wellington/1/2004(H3N2) and B/Shanghai/361/2002. These are the three prototype strains selected for the southern hemisphere 2005 winter season. The vaccine contains purified surface antigens from the three viruses, standardised at 2.5 μg HA per dose for each strain. The vaccine contains an aluminum-based adjuvant and no preservative. The vaccine is applied the tips of the needles of a microprojection array device.

Children who have not previously received an influenza shot are selected for receiving immunisation according to the invention. A relatively hair-free patch of skin on a patient's arm is identified, and the microneedles device is applied to that skin. For some children, the skin is lightly abrased prior to application of the device. Pre- and post-immunization sera are tested as described in reference 52.

Adult Immunization

A monovalent vaccine is prepared from a H5N1 reassortant strain derived from the A/Hong Kong/213/2003 strain. The vaccine contains purified surface antigens from the virus, standardized at 2.5 µg HA per dose for each strain. The vaccine contains an aluminum-based adjuvant and no preservative. The vaccine is applied the tips of the needles of a microprojection array device.

Adults aged 50-60 who have previously received at least two yearly influenza shots with the usual H1N1 and H3N2 strains are selected for receiving immunization according to the invention. A relatively hair-free patch of skin on a patient's arm is identified, and the microneedle device is applied to that skin. For some patients, the skin is lightly abrased prior to application of the device. Pre- and post-immunization sera are tested as described in reference 52.

It will be understood that the invention is described above by way of example only and modifications may be made while remaining within the scope and spirit of the invention.

REFERENCES

The Contents of Which are Hereby Incorporated by Reference

[1] Piascik (2003) *J Am Pharm Assoc* (Wash DC) 43:728-30.
[2] Huckriede et al. (2003) *Methods Enzymol* 373:74-91.
[3] WO97/37000.
[4] Brands et al. (1999) *Dev Biol Stand* 98:93-100.
[5] Halperin et al. (2002) *Vaccine* 20: 1240-7.
[6] Tree et al. (2001) *Vaccine* 19:3444-50.
[7] Kistner et al. (1998) *Vaccine* 16:960-8.
[8] Kistner et al. (1999) *Dev Biol Stand* 98:101-110.
[9] Bruhl et al. (2000) *Vaccine* 19:1149-58.
[10] Pau et al. (2001) *Vaccine* 19:2716-21.
[11] http://www.atcc.org/
[12] http://locus.undnj.edu/
[13] WO03/076601.
[14] Halperin et al. (1979) *Am J Public Health* 69:1247-50.
[15] Herbert et al. (1979)*J Infect Dis* 140:234-8.
[16] Chen et al. (2003) *Vaccine* 21:2830-6.
[17] Hehme et al. (2004) *Virus Res* 103:163-71.
[18] U.S. Pat. No. 6,372,223.
[19] U.S. Pat. No. 6,534,065.
[20] Cooper et (2004) *Vaccine* 22:3136-43.
[21] Frey et al. (2003) *Vaccine* 21:4234-7.
[22] Bozkir & Hayta (2004) *Drug Target* 12:157-64.
[23] Zurbriggen et al. (2003) *Expert Rev Vaccines* 2:295-304.
[24] Guebre-Xabier et al. (2003) *J Virol.* 77:5218-25.
[25] Peppoloni et al. (2003) *Expert Rev Vaccines* 1285-93.
[26] Pine et al. (2002) *J Control Release* 85:263-70.
[27] Baldridge et al. (2000) *Vaccine* 18:2416-25.
[28] WO94/19013.
[29] EP-A-0721782.
[30] U.S. Pat. No. 5,292,506,
[31] Williams (1993) *Vet Microbiol* 37:253-262.
[32] Fitzgerald & Needy (1986) *Dev Biol Stand* 64:73-79.
[33] WO01/22992.
[34] Banzhoff (2000) *Immunology Letters* 71:91-96.
[35] WO02/097072.
[36] U.S. Pat. No. 5,948,410.
[37] U.S. Pat. No. 6,334,856.
[38] U.S. Pat. No. 6,503,231.
[39] U.S. Pat. No. 6,611,707.
[40] Lee et al. (2003) *Lab Chip.* 3:164-7.
[41] WO02/085446.
[42] Sebastien et al. (1998) *J Pharm Sci.* 87:922-5.
[43] Barry B W (2001) *Eur J Pharm Sci.* 14:101-14.
[44] Yang & Zahn (2004) *Biomed Microdevices* 6:177-82.
[45] Matriano et al. (2002) *Pharmaceutical Research* 19:63-70.
[46] Lee et al. (2002) *J Pharm Sci* 91:1613-26.
[47] Alain et al, (2002) *J Controlled Rel.* 81:113-9.
[48] Santi et al. (1997) *Pharm Res.* 14:63-6.
[49] Palmer et al. (1975) Advanced laboratory technicals for immunological diagnostic. U.S. Dept. Hlth. Ed. Welfare, P.H.D. Atlanta. Immunology ser. Nr. 6, Procedural guide, Part 2: haemagglutination-inhibition test, 1975, 25-62.
[50] Schild et al. Single radial haemolysis: a new method for the assay of antibody to influenza Haemagglutinin. *Bull.* WHO, 1975, 52, 43-50.
[51] Aymard et al. Diagnostic sérologique rapide de la grippe par la méthode d'hémolyse radiale modifiée et évolution des anticorps, *Path. Biol.* 1980, 28 no 8, 535-539.
[52] Note for guidance on harmonisation of requirements for influenza vaccines. CPMP/BWP/214/96.
[53] *Vaccines.* (eds. Plotkin &. Orenstein) 4th edition, 2004. ISBN 0-7216-9688-0.
[54] Knipe & Howley *Fields Virology* (4th edition, 2001), ISBN 0-7817-1832-5.

I claim:

1. A method of immunizing a patient against an influenza virus comprising steps of:
   (a) selecting a patient that is immunologically naïve to the influenza virus; and
   (b) administering an immunological composition comprising an antigen of the influenza virus to the patient; wherein
   the immunological composition is delivered to the patient's Langerhans cells by microporation using microneedles made from at least one biocompatible polymer, which open pores in the patient's stratum corneum, wherein the microneedles ranges in length from 25 µm to 1 mm. and wherein the influenza virus antigen is in the form of an inactivated virus or a virosome or wherein the influenza virus antigen is produced by a recombinant or synthetic system that does not involve growth of influenza viruses.

2. A method of immunizing a patient against an influenza virus genus and/or subtype comprising steps of:
   (a) selecting a patient that is immunologically naïve to an influenza virus genus and/or subtype; and
   (b) administering an immunological composition comprising an antigen of the influenza virus genus and/or subtype to the patient; wherein
   the immunogenic composition is delivered to the patient's Langerhans cells by microporation using microneedles made from at least one biocompatible polymer, which open pores in the patient's stratum corneum, wherein the microneedles ranges in length from 25 µm to 1 mm. and wherein the influenza virus antigen is in the form of an inactivated virus or virosome or wherein the influenza virus antigen is produced by a recombinant or synthetic system that does not involve growth of influenza viruses.

3. The method of claim 1, wherein the patient is a child aged between 0 and 18 months.

4. The method of claim 2, wherein the patient is: (i) a child aged between 0 months and 12 years; (ii) a teenager aged between 13 and 19years; (iii) a young adult aged between 20 and 35 years; (iv) a middle-aged adult aged between 36-64 years; or (v) a senior aged 65 years or older.

5. The method of claim 1, wherein the immunogenic composition further comprises an adjuvant.

6. The method of claim 1, wherein the immunogenic composition comprises about 15 µg of HA per strain of influenza virus.

7. The method of claim 1, wherein the immunogenic composition comprises between 0.1 and 8 µg of HA per strain of influenza virus.

8. The method of claim 1, wherein the immunogenic composition has a volume of between 0.05 and 0.5 ml.

9. The method of claim 1, wherein microporation is achieved by a microprojection array system.

10. The method of claim 1, wherein the immunogenic composition includes antigens from at least one strain of influenza A virus and/or at least one strain of influenza B virus.

11. The method of claim 1, wherein the immunogenic composition is in the form of an inactivated virus.

12. The method of claim 11, wherein the immunogenic composition is a whole virus, a split virus or viral subunits.

13. The method of claim 2, wherein the immunogenic composition further comprises an adjuvant.

14. The method of claim 2, wherein the immunogenic composition comprises about 15 µg of HA per strain of influenza virus.

15. The method of claim 2, wherein the immunogenic composition comprises between 0.1 and 8 µg of HA per strain of influenza virus.

16. The method of claim 2, wherein the immunogenic composition has a volume of between 0.05 and 0.5 ml.

17. The method of claim 2, wherein microporation is achieved by a microprojection array system.

18. The method of claim 2, wherein the immunogenic composition includes antigens from at least one strain of influenza A virus and/or at least one strain of influenza B virus.

19. The method of claim 2, wherein the immunogenic composition is in the form of an inactivated virus.

20. The method of claim 19, wherein the immunogenic composition is a whole virus, a split virus or viral subunits.

* * * * *

UNITED STATES PATENT AND TRADEMARK OFFICE
CERTIFICATE OF CORRECTION

PATENT NO. : 10,112,979 B2
APPLICATION NO. : 14/673644
DATED : October 30, 2018
INVENTOR(S) : Derek O'Hagan It is certified that error appears in the above-identified patent and that said Letters Patent is hereby corrected as shown below:

In the Claims

Claim 1, Column 8, Line 41, "(b) administering an immunological composition" should read --(b) administering an immunogenic composition--.

Claim 1, Column 8, Line 44, "the immunological composition is delivered" should read --the immunogenic composition is delivered--.

Claim 1, Column 8, Line 48, "ranges" should read --range--.

Claim 1, Column 8, Line 49, "1 mm." should read --1 mm;--.

Claim 1, Column 8, Line 52, "produced by" should read --produced in--.

Claim 2, Column 8, Lines 56-57, "immunologically naïve to an influenza virus" should read --immunologically naïve to the influenza virus--.

Claim 2, Column 8, Line 58, "(b) administering an immunological composition" should read --(b) administering an immunogenic composition--.

Claim 2, Column 8, Line 65, "the microneedles ranges in length from 25 μm to 1 mm." should read --the microneedles range in length from 25 μm to 1 mm;--.

Claim 4, Column 9, Line 8, "19years" should read --19 years--.

Signed and Sealed this
Eleventh Day of December, 2018

Andrei Iancu
*Director of the United States Patent and Trademark Office*